United States Patent [19]

Johnson, Jr.

[11] Plant 4,022

[45] Mar. 8, 1977

[54] STRAWBERRY PLANT

[75] Inventor: Harold A. Johnson, Jr., Watsonville, Calif.

[73] Assignee: Driscoll Strawberry Associates, Inc., Watsonville, Calif.

[21] Appl. No.: 674,472

[22] Filed: Apr. 7, 1976

[51] Int. Cl.[2] ..... A01H 5/03

[52] U.S. Cl. ..... Plt./49

[58] Field of Search ..... Plt./48–49

*Primary Examiner*—Robert E. Bagwill

EXEMPLARY CLAIM

1. The new and distinct variety of strawberry plant herein described and illustrated, and identified by the characteristics enumerated above.

1 Drawing Figure

1

This invention relates to a new and distinct variety of strawberry plant which is the result of a cross of the patented variety known as Driscoll Associates F5, U.S. Plant Pat. No. 2,892 and Driscoll Associates E17, U.S. Plant Pat. No. 3,274.

The seedlings resulting from the aforementioned cross were grown and asexually multiplied in Shasta County, Calif. and tested in the fruiting beds on the property of growers of the Driscoll Strawberry Associates, Inc. Clones of the seedlings were also held at the Propagation Nursery in Shasta County. One plant was selected from the aforementioned group of seedlings and further asexually reproduced in the Shasta County nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

FIG. 1 of the accompanying drawing illustrates plant parts of the new variety, typical in size, shape and color.

A berry in cross section illustrates flesh color and characteristic core cavity. The inflorescence pictured illustrates typical branching and relative size during early July. There are three secondary peduncles present which are typical, plus two ripe berries, a primary and a secondary, ripe at the same time. The secondary berry is equal in size to the primary. Each berry present has a reflexed calyx which is common. The leaf present has bracts originating from the petiole, one being fused together like a funnel. The presence of bracts is not uncommon and when bracts are present, they are often shaped like a funnel. Fig. 1 shows a flower with 6 petals, but 5 is a more common number.

The novel plant is small to medium in size and medium in vigor when given adequate chilling before being transplanted. The variety is considered a spring variety but is capable of producing a consistent crop throughout the cropping season after a winter digging. In relation to other winter planted varieties, such as Driscoll varieties, Heidi, U.S. Plant Pat. No. 3,123, and G4, U.S. Plant Pat. No. 3,286, it should receive more chilling before being transplanted. This amount of chilling gives the new variety enough plant vigor and still enough flower initiation without becoming too vegetative. The crown crop berries are large and showy if the plant vigor is adequate to support this crop. The crop commences in central California during mid-April with the main crop starting during the last of May and

2 continuing until October. The crop during the second fruiting year is earlier than Heidi, but its total production is not as consistently large as Heidi.

This novel plant of the present invention is distinguished from other varieties by its flowers, fruit and plant characteristics. The new plant is darker, lower growing, smaller, more open with fewer crowns per plant than the Heidi variety. The petioles are shorter but the leaflet size is generally equal to Heidi. The leaflet surface is usually less rugose than Heidi and very similar to F5, one of its parents. Bracts are present in both varieties, but funnel shaped only on the new variety. The petiolules are long; even longer than those of Heidi. The common peduncle, as well as the total inflorescence length, is usually shorter than Heidi. Primary flowers are medium large, but have fewer petals than Heidi. Both varieties produce flowers visible above the plant and anthers that produce an abundance of pollen. Pedicels holding the primary berries originate from both the axil of secondary peduncles or from one of the secondary peduncles while the Heidi pedicel originates mainly at the axil. Both varieties have large primary and secondary fruit, but the new variety tends to produce wedge shaped fruit with a double apex and longitudinal shallow furrows giving the fruit a less smooth appearance. The fruit of the new variety is lighter in color with a distinctive calyx that is consistently reflexed and not as large as Heidi. The sepals are fewer in number, more elliptical and produce fewer serrations than does Heidi. The fruit has a very firm flesh and skin, generally firmer than Heidi. The gloss and appearance is not as consistently attractive as Heidi. The new variety is considered a medium runner producer for a spring variety equal to Heidi. The typical strawberry aroma of the fruit is stronger than that of Heidi. The dessert quality is good, equal to that of Heidi, even though the flesh texture may be firmer.

The new variety is more susceptible to the two-spotted mite, and less susceptible to powdery mildew than Heidi. It is more resistant to *Botrytis* than Heidi. Its reflexed calyx contributes to this resistance. It is less susceptible to cracking injury from rain and it is more susceptible to bronzing injury due to thrip injury. It has not been tested against Verticillium or the Red Stele diseases. As a seedling and selection, this variety withstood natural invasions of certain virus components found in central California without losing its ability to produce.

The varietal characteristics of the novel plant, described below in detail, were observed mainly during the first fruiting season in July, but reference is also made to the appearance during the second fruiting year. Observations were made in the Watsonville area of California which is a cool coastal area near the Pacific Ocean. The color terminology is in accordance with Ridgway's Color Standards and Nomenclature (1912 Edition).

*Plants.*—Medium in size and open; vigorous only if given ample chilling before being planted, and has an extensive root system.

*Leaves.*—Medium to large in size. The central leaflet is usually 6 to 9 cm in length and width. Petioles vary in length, but are usually 18 to 23 cm from the base to the petiolules. Petiolules considered long, 12 mm or longer. Bracts are often present on the petioles and may become a funnel in shape. Leaflet serrations are not noticeably deep or acute at the apex, but are often double with a smaller serration next to the large one. The leaflet serrations often give a premature burned or dying appearance. Leaflet surface not considered strongly rugose, but is smooth with irregular waves over the total surface independent of the leaflet veins. The color of the upper side of the leaflet at Watsonville during July is Dark Cress Green, Plate XXXI.

*Runner.*—Runners are vigorous, but only medium in abundance both at the nursery and the fruiting bed.

*Inflorescence.*—Mostly 20 to 25 cm long. The common peduncle is usually short and three is the most common number of secondary peduncles. Primary and secondary berries often ripen at the same time and secondary berries may equal the primaries in size. Half of the pedicels holding primary berries originate at the axil formed by the union of peduncles and half from one of the secondary peduncles at a point near the axil. Flowers are medium to large in size and produce anthers with an abundance of pollen and usually produce five petals per flower.

*Fruit.*—Crown crop (both first and second year) are generally large in size and amount and are considered early. Fruit from subsequent crops are considered medium to large in size with primaries mostly 40 to 45 mm in length with the width less than the length. Production is relatively uniform through the spring, summer and fall with production starting early for a winter planted spring variety. Fruit shape is irregular medium to long wedge with many berries having a double apex and longitudinal furrows extending from the calyx to the apex. Shoulders are slightly rounded, but not necked even though the calyx is reflexed exposing an area of the fruit where no seed is present. This area around the calyx is often lighter in color than other fruit surface. The apex may also be lighter in color, especially if there is non-fertilized seed present at the tip. The skin and flesh is considered firm. During periods of the fruiting season, the furrows or ribs present may give the fruit a rough appearance. The seeds are medium in size and mostly exerted, yellow, but become dark when exposed to the sun. The dessert quality is good. The fruit surface color is Spectrum Red, Plate I, and the flesh color is Scarlet, Plate I near the perimeter.

*Calyx.*—Medium in diameter with primaries during July averaging 35 to 45 mm in diameter. Sepals are mostly elliptical and primaries have only a slight overlap and are serrated slightly at the apex. The calyx is reflexed. The color of the sepals on the side next to the fruit is Dark Cress Green, Plate XXXI.

I claim:

1. The new and distinct variety of strawberry plant herein described and illustrated, and identified by the characteristics enumerated above.

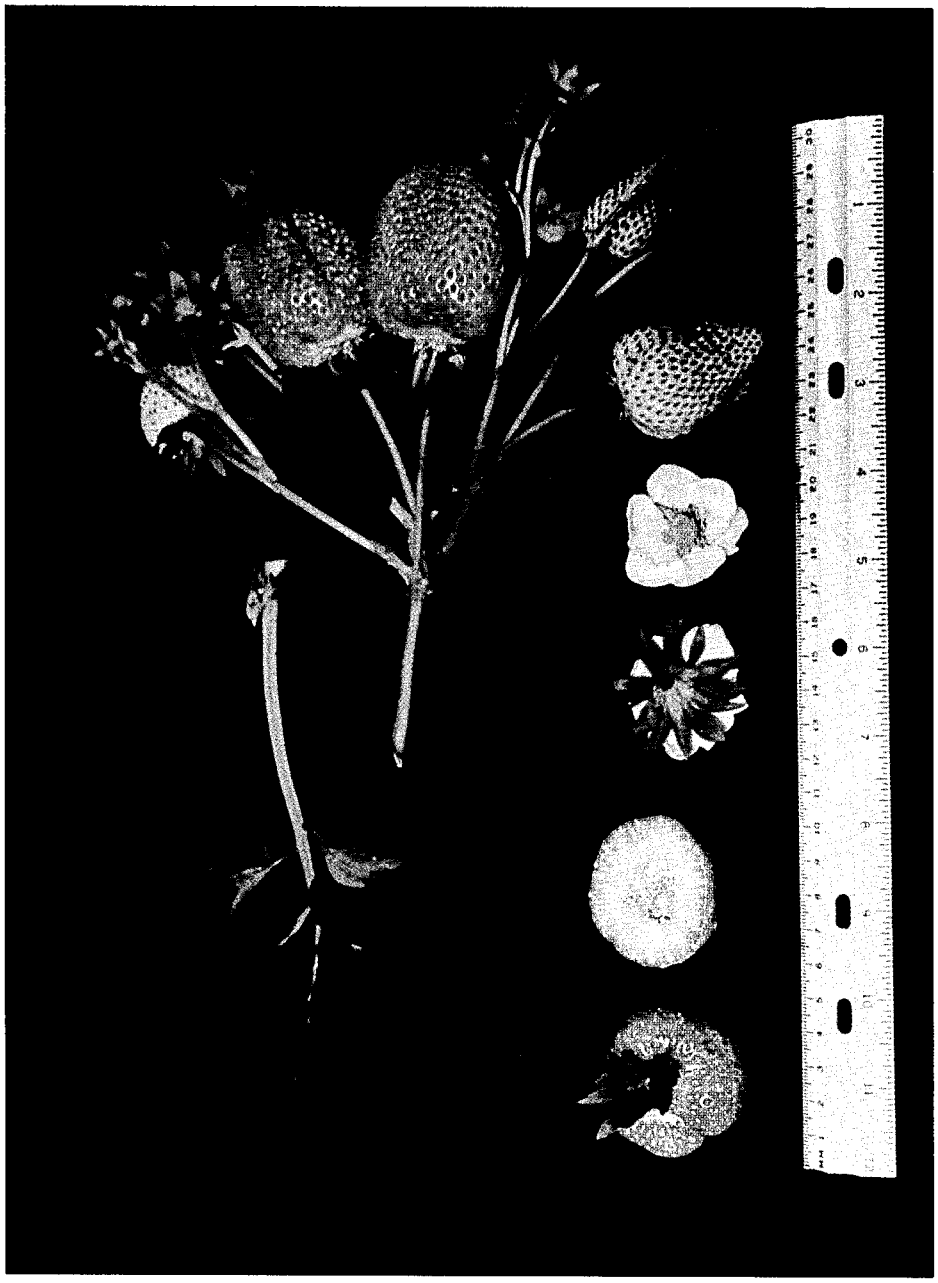

* * * * *